United States Patent
Tanaka et al.

Patent Number: 6,117,686
Date of Patent: Sep. 12, 2000

[54] METHOD FOR DETECTING HARMFUL GASES WHICH IS APPLICABLE TO BROAD GAS CONCENTRATION RANGE

[75] Inventors: Kazunari Tanaka; Chiaki Igarashi, both of Kanagawa-ken; Yoshihiko Sadaoka, Ehime-ken, all of Japan

[73] Assignee: Ebara Corporation, Tokyo, Japan

[21] Appl. No.: 09/365,725

[22] Filed: Aug. 3, 1999

Related U.S. Application Data

[63] Continuation of application No. 08/728,529, Oct. 9, 1996, Pat. No. 5,952,237.

[30] Foreign Application Priority Data

Oct. 18, 1995 [JP] Japan .................................. 7-270290

[51] Int. Cl.⁷ .................................................. G01N 21/77
[52] U.S. Cl. ........................ 436/167; 436/100; 436/101; 436/124; 436/127; 436/163; 436/164; 436/171; 436/181
[58] Field of Search ................................. 436/100, 101, 436/124, 127, 163, 164, 167, 171, 181

[56] References Cited

U.S. PATENT DOCUMENTS

| | | |
|---|---|---|
| 5,018,380 | 5/1991 | Zupancic et al. . |
| 5,319,975 | 6/1994 | Pederson et al. . |
| 5,567,622 | 10/1996 | Jaduszliwer et al. . |
| 5,952,237 | 9/1999 | Tanaka et al. .......................... 436/101 |

FOREIGN PATENT DOCUMENTS

| | | |
|---|---|---|
| 43 32 512 A1 | 3/1995 | Germany . |
| 5-505456 | 8/1993 | Japan . |
| 5-505871 | 8/1993 | Japan . |
| 7-243973 | 9/1995 | Japan . |

OTHER PUBLICATIONS

Journal of Colloid and Interface Science, vol. 124, No. 1, pp. 146–155, Jul. 1988, R. B. Beswick et al, "Optical Detection of Toxic Gases Using Fluorescent Porphyrin Langmuir–Blodgett Films".

Chemical Sensors (Proceedings of the 20th Chemical Sensor Symposium), vol. 11, Supplement A, pp. 93–96, 1995, Yoshihiko Sadaoka et al, "Optochemical HCL and $Cl_2$ Sensor Based on Immobilized Tetra(phenyl)porphyrinates".

Chemistry Letters, pp. 907–908, 1995, Yoshihiko Sadaoka et al, "Optochemical HCL Gas Detection Based on Tetraphenylporphine Dispersed in Ethyl Cellulose".

(List continued on next page.)

*Primary Examiner*—Jan Ludlow
*Attorney, Agent, or Firm*—Oblon, Spivak, McClelland, Maier & Neustadt, P.C.

[57] ABSTRACT

The present invention provides a method by which harmful trace gases in a gaseous mixture containing as such harmful halogen gases, halogenated hydrogen gases, acid gases, oxidizing gases, basic gases, organic acid gases, especially halogen gases or halogenated hydrogen gases, are detected by using tetraphenylporphyrin (TPP) and quantitated from a calibration curve constructed therefrom, where the range of detectable concentration is made adjustable so that harmful gas can be detected and quantitated over a broad range of concentration. Furthermore, this invention also provides a method for extending the accessible range of gas concentration by adjusting the sensitivity of the detector material via control of tetraphenylporphyrin concentration in matrix polymer of the detector material, by controlling the gas concentration range via measurement at a specific wavelength(s), and by the use of a plurality of detector materials with pre-set assay sensitivity.

12 Claims, 5 Drawing Sheets

OTHER PUBLICATIONS

Chemistry Letters, pp. 509–510, 1995, Yoshihiko Sadaoka et al, "Optochemical HCL Gas Detection Based on Zinc Tetrabromotraphenylporphyrin Dispersed in Ethyl Cellulose".

ICCOSS XII, 12$^{th}$ International Conference on the Chemistry of the Organic Solid State, Jul. 9–14, 1995, Okudogo, Matsuyama, Japan, Program and Abstracts, p. 146, Pietro Tagliatesta et al, "Optochemical HCL and CI$_2$ Gas Detection Based on Tetraphenyl Porphinates Dispersed in Ethylcellulose".

Proceedings of the 22$^{nd}$ Chemical Sensor Symposium, Apr. 3–4, 1996, Tokyo University of Agriculture and Technology, pp. 69–72, Kazunari Tanaka et al, "Optochemical Acidic Gas Sensor Based on Tetraphenylporphyrinates Dispersed in Ethylcellulose".

2$^{nd}$ European Conference on Optical Chemical Sensors and Biosensors, Apr. 19–21, 1994, Book of Abstracts, p. 130, M.G. Baron et al, "A Kineto–Optical Method for the Determination of Chlorine Gas".

Sensors and Actuators, vol. B29, Nos. 1–3, pp. 358–361, Oct. 1995, Proceedings of the 2$^{nd}$ European Conference on Optical Chemical Sensors and Biosensors, M.G. Baron et al, "A Kineto–Optical method for the Determination of Chlorine Gas".

Inorganic Chemistry, vol. 18, No. 1, pp. 201–206, 1979, A. Giraudeau et al, "Effects of Electron–Withdrawing Substituents on the Electrochemical Oxidation of Porphyrins".

Journal of the American Chemical Society, 101:14, pp. 3857–3862, Jul. 4, 1979, A. Giraudeau et al, "Substituent Effects in the Electroreduction of Porphyrins and Metalloporphyrins".

Inorganic Chemistry, vol. 30, No. 2, pp. 239–245, 1991, P. Bhyrappa et al, "Octabromotetraphenylporphyrin and its Metal Derivatives: Electronic Structure and Electrochemical Properties".

Inorganic Chemistry, vol. 32, No. 19, pp. 4042–4048, 1993, F. D'Souza et al, "Electrochemical and Spectroelectrochemical Behavior of Cobalt(II), and Cobalt(I) Complexs of meso–Tetraphenylporphyrinate Bearing Bromides on the beta–Pyrrole Positions".

Sensors and Actuators B, No. 18–19, pp. 493–496, 1994, A. Morales–Bahnik et al, "An Optochemical Ammonia Sensor Based on Immobilized Metalloporphyrins".

Journal of Physics and Chemistry of Solids, vol. 49, No. 3, pp. 315–321, 1988, Collin L. Honeybourne et al, "The Chemical Degradation of Gas–Sensing Meso–Tetra–Arlyporphin Thin Films by High Levels of Dinitrogen Tetroxide".

Sensors and Actuators B, No. 13–14, pp. 543–544, 1993, M.G. Baron et al, "Optical Thin Films for Gas Sensing".

Sensors and Actuators B, No. 11, pp. 195–199, 1993, M.G. Baron et al, "Luminescent Porphyrin Thin Films for NOX Sensing".

Tagliatesta et al, Moi. Cryst. Liq. Cryst. Sci. Technol., Sect. A (1996), vol. 278, pp. 173–180.

Tanaka et al, J. Mater. Chem. (1996), vol. 6, No. 6, pp. 953–956.

METHOD FOR DETECTING HARMFUL GASES WHICH IS APPLICABLE TO BROAD GAS CONCENTRATION RANGE

This application is a Continuation of application Ser. No. 08/728,529 Filed on Oct. 9, 1996 now U.S. Pat. No. 5,952,237.

FIELD OF THE INVENTION

The present invention relates to a method for detecting harmful gases designed to detect a harmful gas in a gaseous mixture containing at least one member selected from the group consisting of halogen gases, hydrogen halide gases, acidic gases, oxidizing gases, basic gases and organic acid gases or, more specifically, relates to a novel method of detecting the above-mentioned gases by specific tetraphenylporphyrin.

PRIOR ART

Various means for detecting a harmful gas contained in a mixture of gases such as air have been proposed. Unlike detection of components in a liquid, it is relatively difficult to detect and quantitate components in a gaseous mixture.

The means of detection currently in common use include (i) detector tubes, (ii) color changing beads, (iii) detection tapes and (iv) electrolysis at constant potential. All these methods, nevertheless, have the following drawbacks:

Measurement is time-consuming;

Sensitivity is in the order of ppm which is not satisfactory; and

Continuous detection is not possible.

PCT WO 91/07659 (Unexamined Japanese Patent Publication No. Hei 5-505871) discloses a gas sensor comprising a gas detector including a component of which color or electro-conductivity changes upon exposure to a certain gas or gases to be detected. The gas detector comprises (mono-, di- or tri-)azatetrabenzoporphyrin which contains chromium (III), vanadium, manganese, cobalt or iron (III) in the porphyrin moiety.

The above gas sensor detects a target gas by virtue of change in color or electro-conductivity of the detector component on exposure to the target gas, but the sensitivity thereof has not proven to be sufficiently high to detect those gases. Although it is claimed therein that some of the detector components exhibit restoration of their gas detection ability to some extent after removal of the gases being detected, it usually takes a substantial time for the sensor to recover its ability. Of the gas sensors disclosed, even that which requires the shortest time for restoration is not at all sufficient for continuous measurement.

There has been a strong demand for a highly sensitive, simple method to rapidly detect harmful components in a gaseous mixture, e.g., air. For example, it is desired that a simple means for rapid detection of harmful components, e.g., halogens or hydrogen halides, in an exhaust gas discharged from a semiconductor manufacturing unit in order to prevent accidental evacuation of such noxious substances into the atmosphere.

RELATED ART

Recently, the present inventors have found that tetraphenylporphyrin derivatives with certain substituent groups attached to the porphyrin ring and their metal complexes are pigments that are reactive with harmful gases such as halogen gases, hydrogen halide gases, acidic gases and oxidizing gases. In the Specifications of Unpublished Japanese Patent Application No. 85988/95 filed on May 20, 1995, the present inventors have disclosed a method wherein the spectrum change of the gas-reactive pigment upon contact with a halogen gas, hydrogen halide gas or the like is determined by way of light which is reflected from or transmitted through the detector and the change is plotted as a function of gas concentration to obtain a calibration curve so that the concentration of the target gas can be quantitatively detected.

Conventionally, simple and reliable methods for detecting trace components in a gaseous mixture (including that which is disclosed in the foregoing specification) are based, e.g., colorimetry. Such methods comprise preparing a calibration curve with respect to color change vs gas concentration, applying the detected color change to the curve, and determining the concentration of the target gas.

However, it has been found that, in the method where the concentration of a halogen gas or hydrogen halide gas is measured by way of changes in the color intensity or the peak height in the absorption or reflective spectrum at a specific tetraphenylporphyrin wavelength, the range between the test gas concentration at which a peak height begins to change upon contact with said gas and that at which the change reaches a plateau is fairly narrow, often making it impractical to prepare a calibration curve over a broad gas concentration range.

Not infrequently in the procedure, therefore, a gas concentration range covered by a calibration curve for a given gas does not coincide with the gas concentration range in the practical determination. This makes it necessary to include an extra step of diluting or concentrating the subject gas to a concentration appropriate for the calibration curve. Accurate adjustment of a gas concentration entails difficulties and it is extremely difficult to conduct continuous measurement of a test gas if such a gas concentration adjustment step is required.

Thus the present inventors have described a method in the Specification of Unpublished Japanese Patent Application No. 85988/95, wherein the concentration of a harmful gas such as halogen gas, hydrogen halide gas, acidic gas or oxidizing gas, is quantitatively determined using a calibration curve prepared from the changes in color intensity of a gas-reactive pigment on contact with the harmful gas plotted against known standard concentrations of the gas. The tetraphenylporphyrin used in this method quickly restores the initial state when the harmful gas is removed from the assay system.

SUMMARY OF THE INVENTION

It is an object of the present invention to provide a method for detecting and quantitating a trace amount of a harmful gas in a gaseous mixture by the use of tetraphenylporphyrin, wherein said harmful gas is selected from halogens, hydrogen halides, acidic gases, oxidizing gases, basic gases and organic acid gases, especially halogens and hydrogen halides.

Harmful gases to be detected such as halogen gases, hydrogen halide gases, acidic gases, oxidizing gases, basic gases and organic acid gases may hereinafter be referred to simply as "halogens or hydrogen halides".

DETAILED DESCRIPTION OF THE INVENTION

The present inventors conducted an extensive study with respect to the position and height of the spectrum peak at a specific wavelength in the transmission or reflection light from a detector having a layer of matrix polymer comprising tetraphenylporphyrin, while the detector is being contacted with a gaseous mixture which contains at least one harmful gas from halogen gases, oxidizing gases, basic gases and organic gases under light irradiation, and they have made the following discovery.

That is, when the concentration of tetraphenylporphyrin contained in the matrix polymer is increased, a new absorption peak appears at the approximate wavelength of 718 nm not disclosed in the aforementioned Japanese Patent Application No. 85988/95. Furthermore, it has also been discovered that when the concentration of tetraphenylporphyrin in the matrix polymer is altered, the gas concentration at which the spectrum peak (either at 718 nm or 450 nm) begins to appear due to reaction with the detector also changes, as measured in terms of transmittance or reflection light from the detector at a specific wavelength. For example, the spectrum peak begins to appear at a higher gas concentration in the determination with a detector containing a lower concentration of tetraphenylporphyrin, whereas the spectrum peak begins to appear at a lower gas concentration in the determination made using a detector containing a higher concentration of the pigment. These newly discovered phenomena are observed specifically with tetraphenylporphyrin.

By taking advantage of these phenomena, it is possible to detect and quantitate harmful gases over a broader range of concentration than by the conventional system via the use of plural detectors containing tetraphenylporphyrin in different concentrations in a matrix polymer. The present invention has been accomplished on the basis of these findings.

In one aspect, the present invention is a method of measuring harmful gas comprising the steps of:
  providing a detector consisting of a polymer matrix which comprises tetraphenylporphyrin (TPP) represented by the following formula (1):

and which if necessary, may be supported on a substrate, e.g., by being coated thereon;
  irradiating the detector while the detector is being exposed to a gaseous mixture suspected of containing a harmful gas or gases selected from the group consisting of halogen gases, hydrogen halide gases, acidic gases, oxidizing gases, basic gases and organic acid gases;
  measuring the peak height of the absorption spectrum of TPP at a particular specific wavelength in the transmitted or reflected light from the detector; and
  determining the level of the harmful gas in said gas mixture based on the height of the peak;
  wherein the concentration range of the harmful gas in the gaseous mixture which is detectable by a detector containing TPP at a particular concentration is predetermined with respect to several TPP concentrations, and the measurement is conducted by a detector which contains TPP at an appropriate concentration depending on the concentration of the harmful gas in the gaseous mixture, whereby the necessity for a dilution step of the gaseous mixture before measurement is reduced or removed.

Preferably two or more detectors made from polymer matrix containing different concentrations of tetraphenylporphyrin are used in the method of the present invention. The concentration of tetraphenylporphyrin in the polymer matrix of each detector depends on the concentration of the harmful gas to be measured and/or the wavelength at which the measurement is conducted. These detectors may be used independently in the measurement, although simultaneous use is preferred.

Tetraphenylporphyrin used in the invention is commercially available, but if necessary said compound can be produced in accordance with the method described, for example, in "A Simplified Synthesis for meso-tetraphenylporphin," Adler, Alan D.; Longo, Frederick R. J. Org. Chem. 1967, 32, 476 and "High-Performance Thin Layer Chromatography of Metal. Tetraphenylporphyrin Chelates", K. Saitoh, M. Kobayashi, N. Suzuki, Anal. Chem., 53. 2309 (1981).

Reproducibility of an assay is highly important in determining the concentration of a harmful gas in a test specimen by virtue of color change or development. In general, in order to ensure satisfactory reproducibility, conventional assays of this kind have been conducted as follows. First, the spectrum peaks of the detector are identified in the light from the test detector which is under irradiation at varying wavelengths, e.g., by observing the absorbance/reflectance spectrum of the detector. There-after, the color intensity of the detector is measured while it is being irradiated at one of the wavelengths of the spectrum peaks in the presence of the gas to be detected.

In contrast, in the method of the present invention, the concentration of harmful gas is determined based on the height of the peak of absorption or reflection spectrum at a specific wavelength, wherein said peak is characterized in that it appears as a result of the reaction of tetraphenylporphyrin of formula (1) with a harmful gas and that the existence or non-existence and height of said peak are dependent on the concentration of TPP of formula (1) in the matrix of the detector as well as the kind and concentration of the harmful gas. Thus, the detector used in the present invention is so selected that it contains an appropriate concentration of tetraphenylporphyrin depending on the kind and concentration of the harmful gas to be detected. That is, the concentration of tetraphenylporphyrin in the detector employed in the invention will be varied so as to adjust it to the kind and concentration of the harmful gas in the gas mixture.

More specifically, several detectors varying in tetraphenylporphyrin (TPP) concentrations in the matrix were prepared. These detectors were exposed to gaseous mixtures containing various concentrations of a hydrogen halide (gas to be detected) and a spectrometric analysis (FIGS. 2 and 3) was made under light irradiation using a gas detection apparatus illustrated in FIG. 1.

As a result of the measurement made on the light which was reflected from the detector, a new absorption peak was observed at a specific wavelength (ca. 718 nm) in the scanning of incident light. Importantly, this peak appeared only when the detector contained a certain level of tetraphenylporphyrin (TPP) or higher, although said peak was not observed at lower TPP concentrations. The size of the new peak increased in a dose-dependent manner on TPP concentration. Furthermore, it was found that "the range of a harmful gas concentration wherein the height of said new peak exhibits a dose-dependent relation between the gas concentration" can be controlled by appropriately selecting the amount of TPP contained in the detector. That is, it was found to be possible to prepare a detector with a desired sensory range. This is typically illustrated in FIG. 5.

In other words, when reflectance was measured at the specific wavelength, in the light from said detector, the range of target gas concentrations within which the reflectance changes in a dose dependent manner shifted in accordance with the concentration of TPP contained in the detector matrix. According to the study of the present inventors, the range of target gas concentrations within which light reflectance changes shifts progressively to a lower side with an increasing concentration of TPP contained in the matrix.

Therefore, the present invention takes advantage of said particular wavelengths. That is, by providing a plurality of detectors with varying TPP concentrations (i.e., with preselected sensory ranges), it is possible to select an appropriate detector to accomplish accurate measurement of the concentration of target gas without any need of a prior dilution or concentration of the gas mixture. In other words, the measurable range of harmful gas concentrations is expanded.

In accordance with a preferred embodiment of the present invention, the gas concentration range measurable by the method can be further extended by use of a plurality of detectors whose sensory ranges are adjusted as described in detail above. Such an embodiment will be given in Example 3.

The concentration of TPP in the detector used in the method provided by the present invention thus is preferably about $1 \times 10^{-5}$ to $6 \times 10^{-5}$ mol/g matrix.

Accordingly, the detector contains a lower concentration of tetraphenylporphyrin for a gaseous mixture with a higher concentration of harmful gas, whereas the detector contains a higher concentration of tetraphenylporphyrin for a gaseous mixture with lower concentration of harmful gas.

Therefore, in another aspect of the present invention, the method of measuring harmful gas is provided, which comprises the steps of: providing a detector comprising tetraphenylporphyrin (TPP) represented by the formula (1) in a polymer matrix, which may be supported on a substrate;

irradiating the detector with light while the detector is being contacted with a gaseous mixture which is suspected of containing at least one harmful gas selected from the group consisting of halogens, hydrogen halides, acidic gases, oxidizing gases, basic gases and organic acid gases;

measuring peak heights of the absorption spectrum of TPP at approximate wavelengths of 450 nm and 718 nm in the light which is transmitted or reflected from the detector;

preparing a first calibration curve which plots heights of the absorption peak of TPP at an approximate wavelength of 450 nm under known concentrations of the harmful gas to be detected;

preparing a second calibration curve which plots heights of the absorption peak of TPP at an approximate wavelength of 718 nm under known concentrations of the harmful gas to be detected;

applying the peak height measured at ca. 450 nm to the first calibration curve and applying the peak height measured at ca. 718 nm to the second calibration curve, whereby to determine the concentration of the harmful gas to be detected.

In this embodiment, the first calibration curve covers a lower concentration range of a harmful gas and the second calibration curve covers a higher concentration range of harmful gas, whereby the measurable concentration range of a harmful gas will be broader than methods wherein the measurement is conducted at a single wavelength. Further, the detector for the measurement at the approximate wavelength of 718 nm will contain a greater concentration of TPP than the detector used for the measurement at the other wavelength.

Production of Gas Detector

The detector used in the method of the present invention may be prepared by mixing TPP with a transparent matrix polymer and applying the mixture on a substrate for the detection of harmful gases such as halogen gases, hydrogen halide gases, acidic gases, oxidizing gases, basic gases and organic acid gases. For example, TPP is dispersed in a transparent high polymer, such as ethyl cellulose, which shows no significant absorption peak in the region of the absorption wavelength of TPP, and the resultant mixture is applied on the substrate.

As for the matrix polymer used to support TPP on the substrate of a detector of the invention, there is no particular limitation insofar as it is a high polymer preferably soluble in a solvent common to that for TPP, and it is at least translucent or, more preferably, transparent, thus having no significant absorbance peak at the absorption wavelength of the gas-reactive pigment.

Nafion, ethyl cellulose, ethoxyethyl cellulose, cellulose acetate, cellulose acetate butyrate, modified starch, polyvinylpyrrolidone, vinylpyrrolidone copolymer, polymethyl vinyl ether and methyl vinyl ether copolymer may be mentioned as examples of the high polymer.

Nonlimiting examples of the solvents for these matrix polymers include toluene, ethanol, toluene/ethanol mixture, dioxane, dimethylformamide, acetone and other organic solvents.

Examples of the substrates or carriers on which the gas-reactive pigment mixed with the aforementioned matrix polymer is supported include alumina, glass, optical fiber, paper, glass beads and silica gel, although the invention is not limited thereto.

Gas Detection Apparatus

Figure 1:
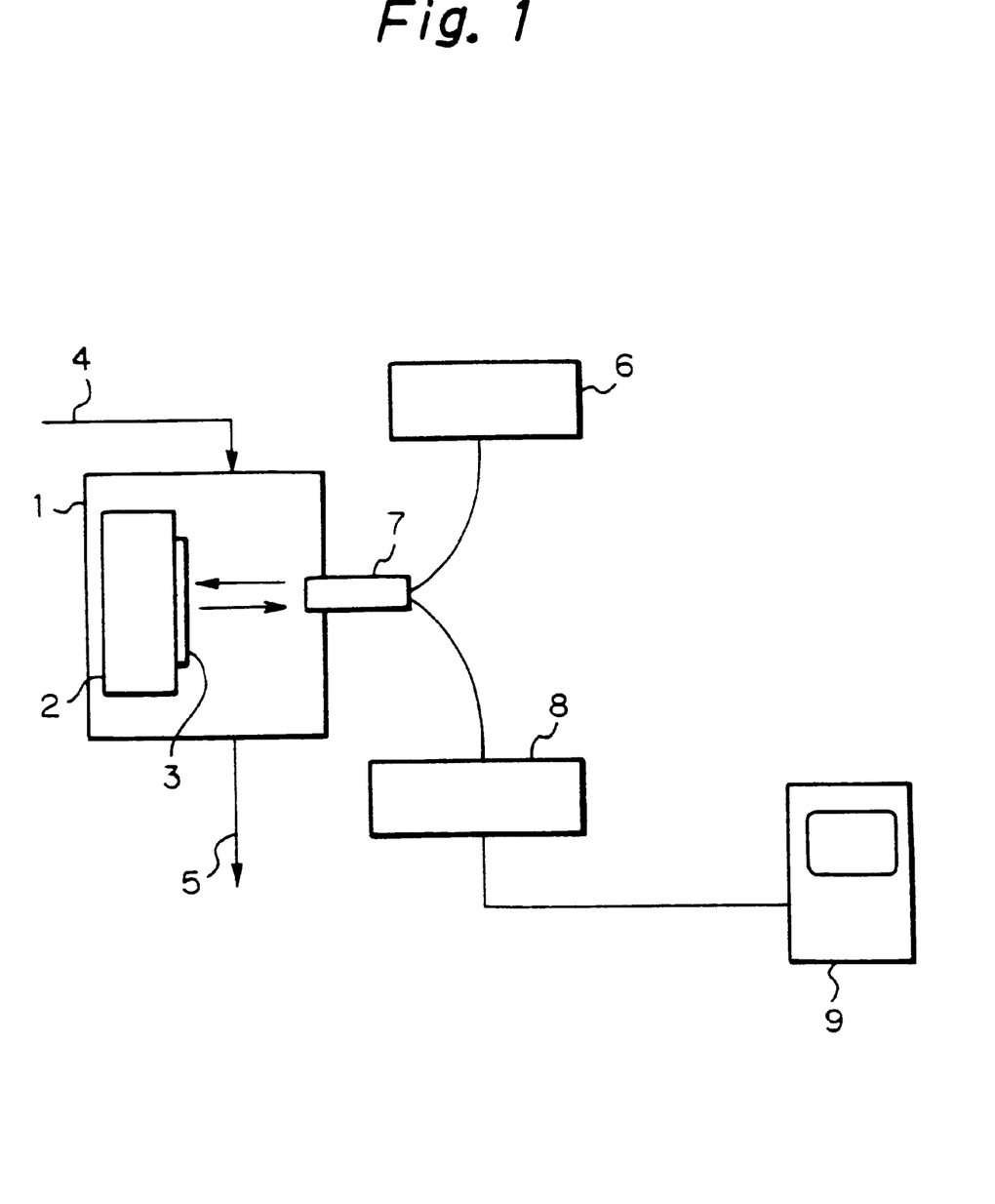
FIG. 1 is a schematic representation of an example of the light reflection type detector provided by this invention, where 1 is a measurement cell; 2, substrate; 3, detector; 4, gas to be detected; 5, exhaust gas; 6, halogen lamp; 7, projector/receptor; 8, photomultiplier; and 9, computer.

In accordance with the present invention, as illustrated in FIG. 1, detector (3) is prepared by applying a solution of TPP and ethyl cellulose in a solvent on substrate (2) and drying the solvent. The detectors are mounted in measuring cell (1) of the detection apparatus. Projector/receptor unit (7) is provided. A light beam from halogen lamp (6) is led through an optical fiber to vertically irradiate detector (3) by way of the projector. The light reflected by substrate (2) of the detector (3) is caught by the receptor, from which the signals are transmitted to photomultiplier (8). Gas to be detected (4) is passed into the measuring cell (1) and the changes in the reflection spectrum of TPP resulting from the reaction thereof with the gas is measured with photomultiplier (8). The resulting data are introduced into and processed by computer (9).

Another type of detection apparatus, though not shown in the drawings, may comprise, for example, a gas duct wherein gas containing hydrogen chloride to be detected is passed through, and a detector provided in the duct and composed of an optical fiber prepared by coating a solution of TPP and ethyl cellulose thereon and drying the solvent. A light beam from a halogen lamp is introduced to the optical fiber and the reflected beam from the optical fiber is detected by a photomultiplier.

It will be apparent for those skilled in the art that either of the above apparatus has a plurality of detectors.

Also, a detection apparatus of the invention may be so designed as to combine both these embodiments in a single unit.

It has been observed that the color change of the gas reactive pigment (TPP) upon reaction with a hydrogen halide gas does not take place uniformly throughout the wavelengths of the spectrum. Comparison of the reflective spectra before and after the reaction reveals that, in general, appreciable changes take place at specific wavelengths.

The present invention will be further illustrated by the following examples. Needless to say, it is not intended that the scope of the present invention be limited to these examples.

Example 1

Figure 2:
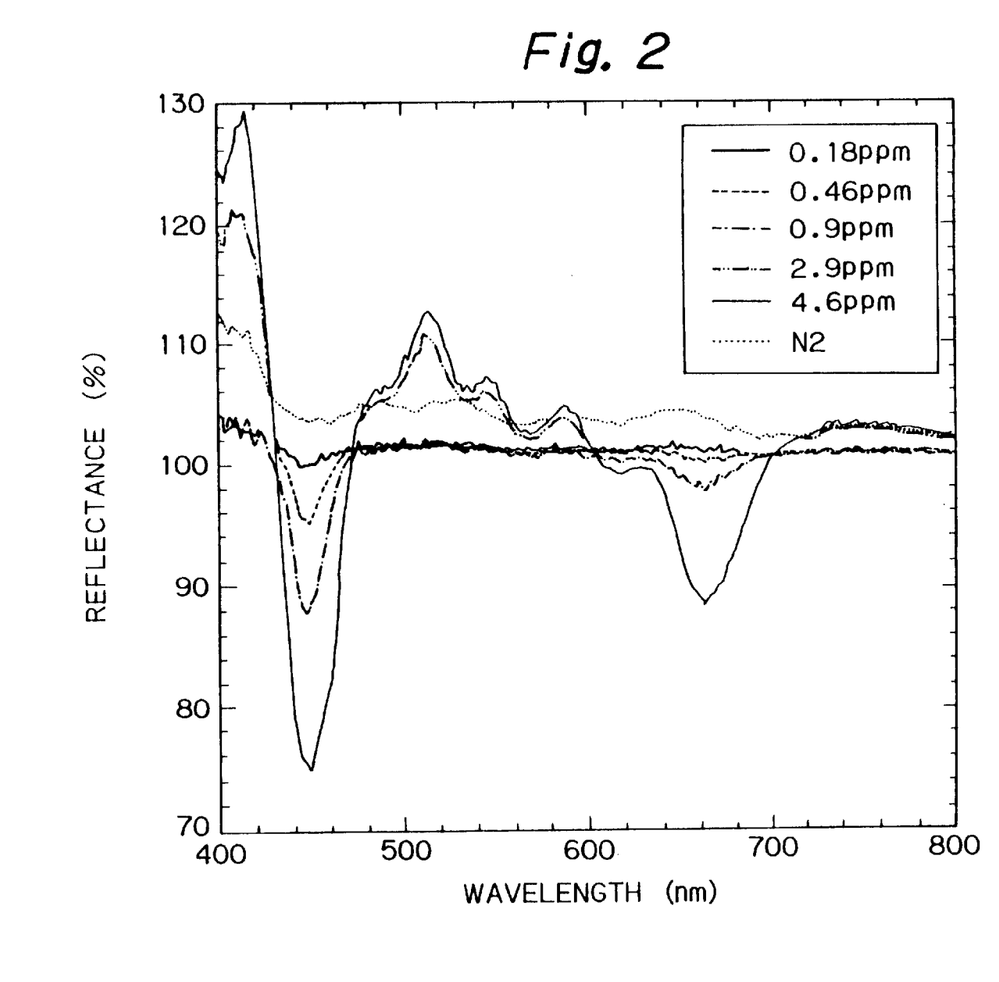
FIG. 2 illustrates the changes in reflectance in response to varying hydrogen chloride levels in a gas mixture which is brought into contact with the detector comprising TPP (chlorine free) at a concentration of $1.6 \times 10^{-5}$ mol/g in ethyl cellulose. The reflectance is depicted as the spectrum scanned over the wavelengths from 400 to 800 nm.

Using ethyl cellulose for example as a matrix polymer, a detector was prepared by mixing $1.6 \times 10^{-5}$ mol/g tetraphenylporphyrin (TPP) (purchased from Tokyo Kasei Kogyo Co. Ltd., Tokyo, Japan) as a coloring reagent with ethyl cellulose in a solvent, applying the mixture onto a glass substrate and drying the solvent. The detector so prepared was then mounted in a measuring cell of the detection apparatus shown in FIG. 1. $N_2$ gas containing 0.18, 0.46, 0.9, 2.9 or 4.6 ppm of hydrogen chloride was passed into the measuring cell to allow it to get contact with TPP, and the reflectance thereof (expressed as percent of background value) at various wavelengths was measured against $N_2$ gas alone as the background. Results obtained are shown in FIG. 2. As can be seen, the assay sensitivity is increased when the measurement is carried out at the wavelength showing the peak (i.e., prominent change).

Example 2

Figure 3:
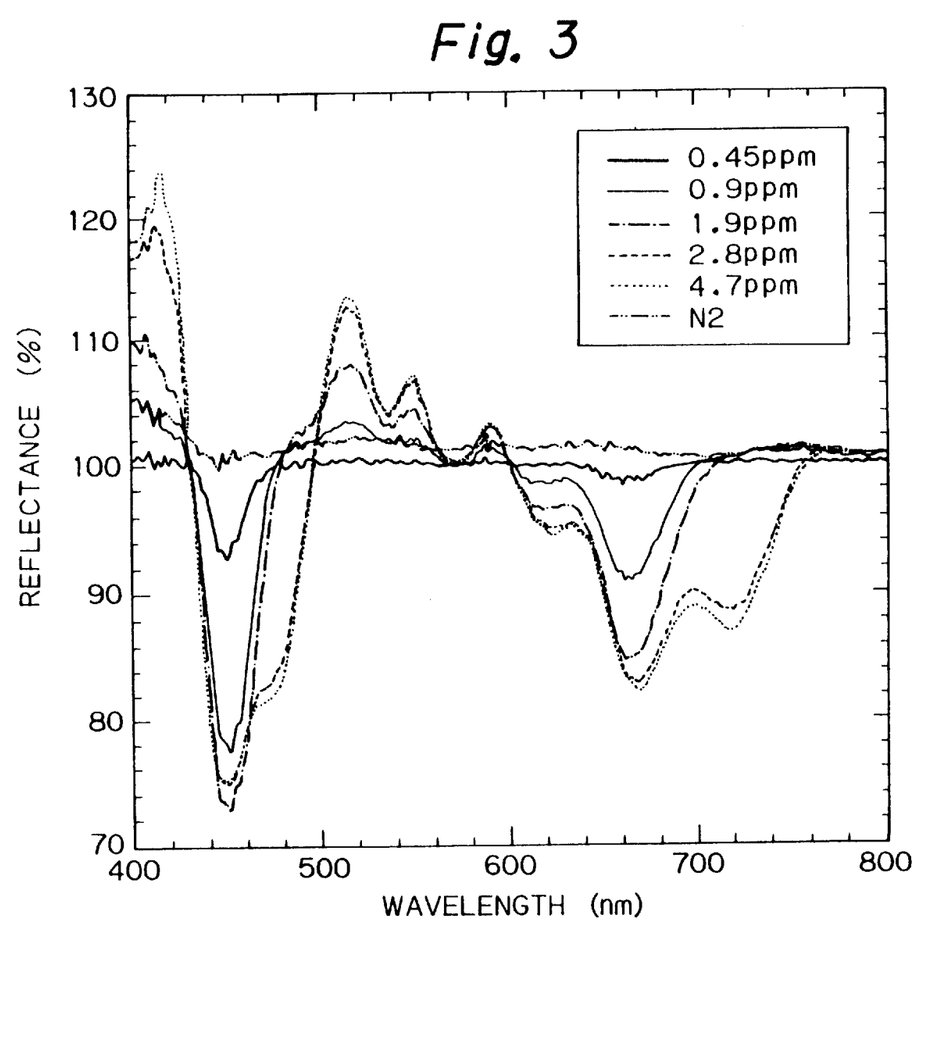
FIG. 3 illustrates the changes in reflectance in response to varying hydrogen chloride levels in a gas mixture which is brought into contact with the detector comprising TPP (chlorine free) at a concentration of $3.3 \times 10^{-5}$ mol/g in ethyl cellulose. The reflectance is depicted as the spectrum scanned over the wavelengths from 400 to 800 nm.

FIG. 3 depicts changes in the reflectance spectrum as measured with a detector composed of $3.3 \times 10^{-5}$ mol/g TPP in ethyl cellulose on contact with 0 to 4.6 ppm of hydrogen chloride.

When the data in this figure are compared with those in FIG. 2, it can be noted that the reflectance peak nonexistent at 718 nm in FIG. 2 was observed in the measurement made using the detector containing $3.3 \times 10^{-5}$ mol/g TPP in ethyl cellulose (hence the detector of this example is more sensitive than the detector used in Example 1).

Example 3

A. Nitrogen gas containing 0.18 to 2.9 ppm of hydrogen chloride was passed into a measuring cell of the detection apparatus illustrated in FIG. 1 and the reflectance at 450 nm was determined using a detector containing $1.6 \times 10^{-5}$, $3.3 \times 10^{-5}$ or $6.3 \times 10^{-5}$ mol/g TPP in ethyl cellulose (EC).

B. Nitrogen gas containing 0.18 to 4.5 ppm of hydrogen chloride was passed into a measuring cell of the detection apparatus illustrated in FIG. 1 and the reflectance at 718 nm was determined using a detector containing $1.6 \times 10^{-5}$, $3.3 \times 10^{-5}$ or $6.3 \times 10^{-5}$ mol/g TPP in ethyl cellulose (EC).

Figure 4:
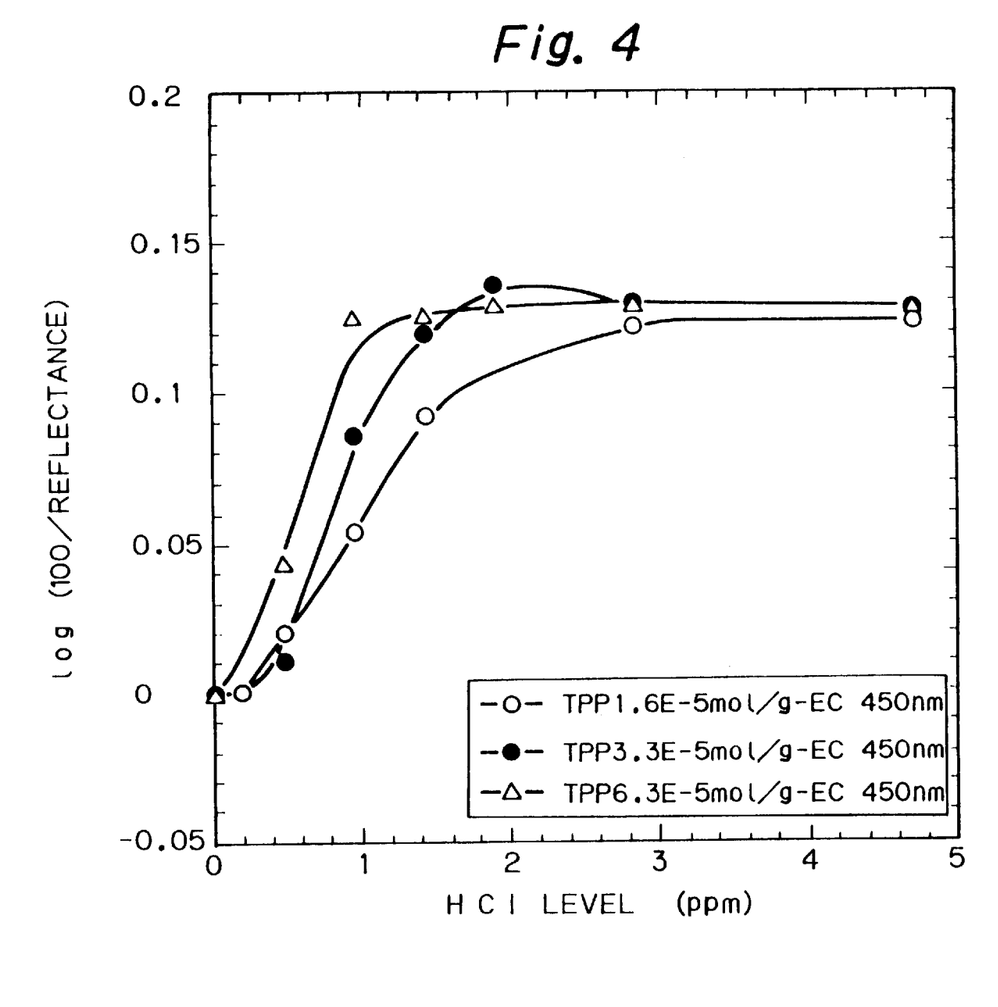
FIG. 4 is a graph depicting log(100/reflectance) versus hydrogen chloride gas concentration as determined under irradiation at 450 nm using detectors having TPP (chlorine free) in varying concentrations.
Figure 5:
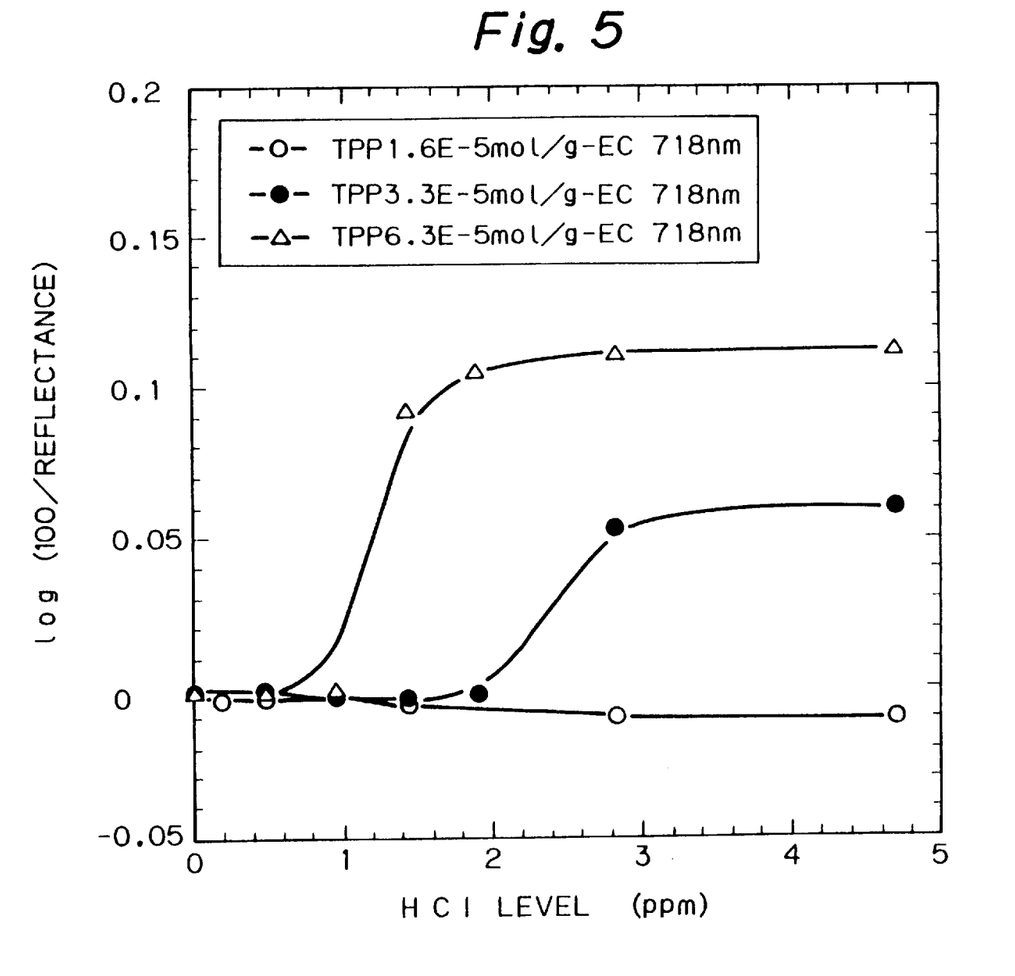
FIG. 5 is a graph depicting log(100/reflectance) versus hydrogen chloride gas concentration as determined under irradiation at 718 nm using detectors having TPP (chlorine free) in varying concentrations.

FIG. 4 shows the relation of log(100/reflectance) versus concentration of hydrogen chloride plotted on the basis of the data obtained in Example 3A. FIG. 5 depicts a similar relation plotted based on the data from Example 3B.

With the use of the detector comprising $1.6 \times 10^{-5}$ mol/g TPP in EC, hydrogen chloride can be detected only in a concentration range from 0.18 to 1.5 ppm by reference to the graph in FIG. 4 as the calibration curve. Whereas, if the detector composed of $3.3 \times 10^{-5}$ mol/g TPP in EC is used simultaneously, hydrogen chloride can be detected over a broader concentration range from 0.18 to 2.8 ppm by referring to both the graph in FIG. 4 and that in FIG. 5 plotted from the data obtained at the wavelength of 718 nm.

In accordance with the method of the invention for detecting target gas concentration, the detectable range of target gas concentration can be predetermined by controlling the sensitivity of the detector by way of the concentration of tetraphenylporphyrin in the matrix polymer, and by making the measurement at the specific wavelengths.

The detectable range of target gas concentration thus can be broadened via the use of a plurality of detectors of which assay sensitivities have been adjusted in accordance with the disclosure of the invention. This feature endows the practical value with the method for detecting gas concentration provided by the present invention.

What is claimed is:

1. A method of measuring the concentration of a harmful gas, comprising:

(a) irradiating a single detector with a first light and a second light, said detector being in contact with a gaseous mixture;

wherein said first light comprises a wavelength of about 450 nm and said second light comprises a wavelength of about 718 nm;
wherein said gaseous mixture may contain at least one harmful gas selected from the group consisting of halogen gas, hydrogen halide gas, acidic gas, oxidizing gas, basic gas and organic acid gas; and
wherein said detector comprises, in a polymer matrix, at least $1.6 \times 10^{-5}$ mol/g matrix of tetraplhenylporphyrin (TPP) represented by the following formula:

in a polymer matrix;
(b) measuring a first peak height of the absorption spectrum of TPP in the first light which is transmitted or reflected from said detector;
(c) measuring a second peak height of the absorption spectrum of TPP in the second light which is transmitted or reflected from said detector;
(d) determining a concentration of the harmful gas in said gas mixture based on at least one of the first and second peak heights;
wherein a range of the harmful gas concentration obtained by measuring both of said first and second peak heights is greater than that obtained by measuring either of said first or second peak heights alone.

2. The method as claimed in claim 1, wherein said detector comprises about $3–6.5 \times 10^{-5}$ mol/g matrix of TPP.

3. The method as claimed in claim 1, wherein said detector comprises about $3 \times 10^{-5}$ mol/g matrix of TPP.

4. The method as claimed in claim 1, wherein said detector comprises about $6 \times 10^{-5}$ mol/g matrix of TPP.

5. The method as claimed in claim 1, wherein said detector comprises about $6.5 \times 10^{-5}$ mol/g matrix of TPP.

6. The method as claimed in claim 1, wherein said polymer matrix is supported on a substrate.

7. A method of measuring the concentration of a harmful gas, comprising:
(a) irradiating a single detector with a first light and a second light, said detector being in contact with a gaseous mixture;
wherein said first light comprises a wavelength of about 450 nm and said second light comprises a wavelength of about 718 nm;
wherein said gaseous mixture may contain at least one harmful gas selected from the group consisting of halogen gas, hydrogen halide gas, acidic gas, oxidizing gas, basic gas and organic acid gas; and
wherein said detector comprises, in a polymer matrix, at least $1.6 \times 10^{-5}$ mol/g matrix of tetraphenylporphyrin (TPP) represented by the following formula:

(b) measuring a first peak height of the absorption spectrum of TPP in the first light which is transmitted or reflected from said detector;
(c) measuring a second peak height of the absorption spectrum of TPP in the second light which is transmitted or reflected from said detector;
(d) preparing a first calibration curve by plotting a height of an absorption peak of TPP at an approximate wavelength of 450 nm under known concentrations of the harmful gas to be detected;
(e) preparing a second calibration curve by plotting a height of an absorption peak of TPP at an approximate wavelength of 718 nm under known concentrations of the harmful gas to be detected;
(f) applying said first peak height to said first calibration curve to obtain a first reading, and applying said second peak height to said second calibration curve to obtain a second reading;
(g) determining a concentration of the harmful gas in said gas mixture based on at least one of said first or second readings;
wherein a range of the harmful gas concentration obtained by measuring both of said first and second peak heights is greater than that obtained by measuring either of said first or second peak heights alone.

8. The method as claimed in claim 7, wherein said detector comprises about $3–6.5 \times 10^{-5}$ mol/g matrix of TPP.

9. The method as claimed in claim 7, wherein said detector comprises about $3 \times 10^{-5}$ mol/g matrix of TPP.

10. The method as claimed in claim 7, wherein said detector comprises about $6 \times 10^{-5}$ mol/g matrix of TPP.

11. The method as claimed in claim 7, wherein said detector comprises about $6.5 \times 10^{-5}$ mol/g matrix of TPP.

12. The method as claimed in claim 7, wherein said polymer matrix is supported on a substrate.

* * * * *